United States Patent
Kim et al.

(10) Patent No.: US 7,276,501 B2
(45) Date of Patent: Oct. 2, 2007

(54) 6-(4-SUBSTITUTED-ANILINO)PYRIMIDINE DERIVATIVES, METHOD FOR PREPARATION THEREOF AND ANTIVIRAL PHARMACEUTICAL COMPOSITION COMPRISING THE SAME

(75) Inventors: Jong-Woo Kim, Anyang-si (KR); Sang-Wook Lee, Anyang-si (KR); Geun-Hyung Lee, Yongin-si (KR); Jae-Jin Han, Yongin-si (KR); Sang-Jin Park, Yongin-si (KR); Eul-Yong Park, Anyang-si (KR); Joong-Chul Shin, Yongin-si (KR)

(73) Assignee: B & C Biopharm (KR)

( * ) Notice: Subject to any disclaimer, the term of this patent is extended or adjusted under 35 U.S.C. 154(b) by 184 days.

(21) Appl. No.: 10/508,306

(22) PCT Filed: Mar. 25, 2003

(86) PCT No.: PCT/KR03/00588

§ 371 (c)(1),
(2), (4) Date: May 18, 2005

(87) PCT Pub. No.: WO03/084953

PCT Pub. Date: Oct. 16, 2003

(65) Prior Publication Data

US 2005/0222150 A1    Oct. 6, 2005

(30) Foreign Application Priority Data

Apr. 4, 2002    (KR) .................... 10-2002-0018395

(51) Int. Cl.
*A61K 31/5377* (2006.01)
*C07D 413/14* (2006.01)

(52) U.S. Cl. .................... 514/235.8; 544/121
(58) Field of Classification Search ........... 544/121; 514/235.8
See application file for complete search history.

(56) References Cited

U.S. PATENT DOCUMENTS 3,974,162 A    8/1976    Santilli et al.
5,550,240 A    8/1996    Maho et al.

FOREIGN PATENT DOCUMENTS

WO    WO92/05158    4/1992
WO    WO99/41253    8/1999
WO    WO 01/47897    7/2001

OTHER PUBLICATIONS

Chisari, Nature, vol. 436, No. 18, Aug. 2005, pp. 930-932.*
Firpi et al., Liver Transpl. Jan. 2003; 9(1); 57-61.*

* cited by examiner

*Primary Examiner*—Rebecca Anderson
(74) *Attorney, Agent, or Firm*—Blackwell Sanders LLP

(57) ABSTRACT

The present invention relates to 6-(4-substituted-anilino)pyrimidine derivatives useful as an antiviral agent, and more particularly novel 6-(4-substituted-anilino)pyrimidine derivatives having an excellent inhibitory effect on replication of Hepatitis C virus; HCV), represented by the following formula I:

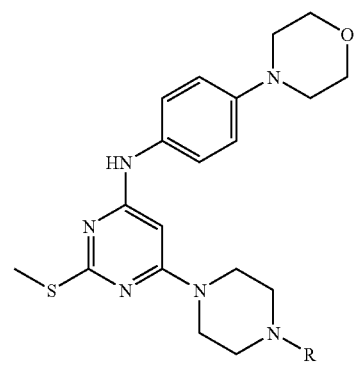

in which R represents a $C_1$-$C_4$ straight or branched alkoxycarbonyl group, heterocycliccarbonyl group or carboxyalkyl group; and pharmaceutically acceptable salts thereof, a preparation method thereof, and an antiviral pharmaceutical composition comprising the compound as an effective ingredient. The 6-(4-substituted-anilino)pyrimidine derivatives according to the present invention have an excellent inhibitory effect on replication of Hepatitis C virus (HCV) and thus can be advantageously used as a therapeutic or prophylactic agent of hepatitis C.

3 Claims, No Drawings

6-(4-SUBSTITUTED-ANILINO)PYRIMIDINE DERIVATIVES, METHOD FOR PREPARATION THEREOF AND ANTIVIRAL PHARMACEUTICAL COMPOSITION COMPRISING THE SAME

This application is a 371 of PCT/KR03/00588 filed Mar. 25, 2003.

1. FIELD OF THE INVENTION

The present invention relates to 6-(4-substituted-anilino) pyrimidine derivatives useful as an antiviral agent, and more particularly novel 6-(4-substituted-anilino)pyrimidine derivatives having an excellent inhibitory effect on replication of Hepatitis C virus (HCV), represented by the following formula I:

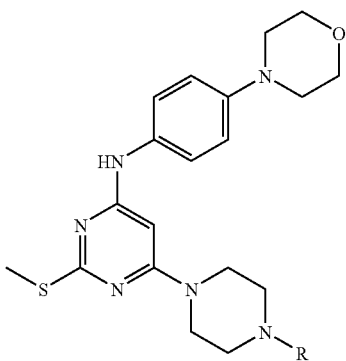

I or pharmaceutically acceptable salts thereof in which R represents a $C_1$-$C_4$ straight or branched alkoxycarbonyl group, heterocycliccarbonyl group or carboxyalkyl group, to a method for preparing the compounds, and to an antiviral pharmaceutical composition comprising the same as an active ingredient.

2. DESCRIPTION OF THE RELATED ART

Hepatitis C virus (HCV) is the major etiological agent of non-A and non-B viral hepatitis, mainly being post-transfusion and community-acquired. Once infected with HCV, approximately 80% of infected people, given its symptom is manifested, progress to chronic hepatitis, and 20% of infected people progress to acute hepatitis causing hepatic cirrhosis, which is eventually transferred to liver cancer. According to a recently published report, more than 200 million worldwide are infected with HCV. For instance, more than 4.5 million Americans are infected with the same virus (The number is likely to be 15 million in maximum.) and more than 5 million Europeans are HCV patients.

HCV is a member of the Flaviviridae family. More specifically, HCV has about 9.5 kb sized (+)-RNA (single stranded positive-sense RNA) genome inside its membrane. The RNA genome consists of an untranslational region at 5' and 3' ends (UTR) and a long open reading frame (ORF). This ORF is expressed as a polyprotein including 3,010 to 3,040 amino acids by host cell enzymes and divided into 3 structural proteins and 6 nonstructural proteins by the host cell and its own protease. Also, there is a uniformly conserved region in the 5' and 3' end of the genome, respectively. This region is believed to play an important role for protein formation and RNA replication of the virus.

The long ORF is expressed as a polyprotein, and through co-translational or post-translational processing, it is processed into structural proteins, i.e. core antigen protein (core) and surface antigen protein (E1, E2), and nonstructural proteins, NS2 (protease), NS3 (serine protease, helicase), NS4A (serine protease cofactor), NS4B (protease cofactor, involved in resistance), NS5A, and NS5B (RNA dependent RNA polymerase, RdRp), each contributing to replication of virus. The structural proteins are divided into core, E1, and E2 by signal peptidase of the host cell. Meanwhile, the nonstructural proteins are processed by serine protease (NS3) and cofactor (NS2, NS4A, and NS4B) of the virus. The core antigen protein together with surface antigen protein of the structural protein compose a capsid of the virus, and the nonstructural proteins like NS3 and NS5B play an important part of the RNA replication of the virus (Reference: Bartenschager, R., 1997, Molecular targets in inhibition of hepatitis C virus replication, Antivir. Chem. Chemother. 8: 281-301).

Similar to other Flaviviruses, the 5' and 3' ends of the virus RNA has a uniformly conserved untranslational region (UTR). Generally, this region is known to play a very important role in replication of the virus. The 5'end has 5'-UTR composed of 341 nucleotides, and this part has the structure of 4 stem and loop (I, II, III, and IV). Actually, this part functions as an internal ribosome entry site (IRES) necessary for translation processing to express protein. Particularly, the stem III, which has the biggest and most stable structure and has a conserved sequence, has been reported to play the most essential part for ribosome binding. In addition, it is known that proteins of the virus are expressed by initiating translation processing from AUG that exists in the single RNA of the stem IV (Reference: Stanley, M. Lemon and Masao Honda, 1997, Internal ribosome entry sites within the RNA genomes of hepatitis C virus and other Flaviviruses, seminars in Virology 8:274-288).

Moreover, the 3' end has 3'-UTR composed of 318 nucleotides. This part is known to play a very important role in initiation step of binding of NS5B, an essential enzyme of RNA replication. The 3'-UTR, according to the sequence and tertiary structure, is composed of three different parts: -X-tail-5' starting from the 5' end to 98th nucleotide (98 nt.), -poly(U)- having UTP consecutively, and the rest of 3'-UTR-. More specifically, X-tail-5' part consists of 98 nucleotides having a very conserved sequence, and has three stem and loop structures, thereby forming a very stable tertiary structure. Probably, this is why X-tail-5' part is considered very essential of NS5B binding. Also, it is reported that -poly(U)- part induces a pyrimidine track, thereby facilitating RNA polymerase effect. Lastly, the rest part of 3'-UTR has the tertiary structure of loop and plays an important role in NS5B binding. However, its structure is somewhat unstable. Overall, the 3'end region of HCV RNA is known to have an essential structure in NS5B binding when the RNA replication starts (Reference: Yamada et al., 1996, Genetic organization and diversity of the hepatitis C virus genome, Virology 223:255-281).

Among other enzymes of HCV, NS5B is the one that is directly involved in RNA replication and thus it is very important. NS5B is an enzyme consisting of 591 amino acids and having molecular weight of about 68 kDa. There are two RNA-binding domains, i.e. RBD1 and RBD2, in the NS5B enzyme. RBD1 exists between the amino acid numbers 83 and 194, and RBD2 exists between the amino acid numbers 196 and 298. Meanwhile, essential motif amino acids for RNA binding and activity are 'Asp' (amino acid number 220), 'Gly' (amino acid number 283), 'Gly' (amino acid number 317), 'Asp' (amino acid number 318), 'Asp' (amino acid number 319), and 'Lys' (amino acid number 346). Further, provided that there exists a RNA template of the virus itself, this enzyme can lead a polymerization reaction without another primer (Reference: Lohmann, V. et al., 1997, Biochemical properties of hepatitis C virus NS5B RNA dependent RNA polymerase and identification of amino acid sequence motifs essential for enzymatic activity, J. viral. 71:8416-8428).

RNA genome of HCV was isolated in 1989 by molecular cloning (Reference: Choo, Q-L, et al., 1989, Isolation of a cDNA clone derived from a blood-borne non-A, non-B viral hepatitis genome. Science 244:359-362). Although there have been a number of molecular biological researches on HCV from that point, there were always limitations due to lack of more effective cell culture systems and animal models. Fortunately, the above problem has been somewhat resolved by the introduction of a hepatoma cell line which made it possible to replicate HCV more stably (Reference: Lohmann, V., F. Korner, J-O Koch, U. Herian, L. Theilmann, R. Bartenschlarger, 1999, Replication of subgenomic hepatitis c virus RNAs in a hepatoma cell line. Science 285:110-113).

So far, no one has actually found vaccine or therapeutics that is very effective for HCV. Hence, many pharmaceutical companies and institutes around the world are now trying to develop therapeutics and prevention of hepatitis C. HCV patients are prevalent in the world, and its frequency to be progressed to hepatic cirrhosis and/or liver cancer is much higher than HBV. Also, despite its high frequency to be progressed to chronic hepatitis, the research on infection mechanism of the virus is still under progress. People are infected with HCV through blood transfusion or medication via phleboclysis or tattooing, but most of cases HCV infection takes place through a direct blood contact. However, 40-50% of the HCV patients still do not exactly know how they became infected. In view of this situation, it is a very urgent matter to develop a new vaccine and therapeutics to treat the diseases. In general, HCV has diverse genotypes between strains and mutation. Once a person is progressed to chronic hepatitis from HCV, it is not hard to see reinfection or coinfection owing to genetic variants. Because of this, few succeeded to develop an effective vaccine for HCV. Another example of HCV treatments is using alpha interferon (α-interferon). However, this approach proved to be not that good because the effects of alpha interferon on different HCV genotypes were very diverse and when its administration was discontinued, patients were relapsed into hepatitis C in most of cases. Hence it will be important to develop an inhibitor that binds only to a particular HCV protein in order to control HCV replication. The best targets of such research are NS3 protease/helicase and NS5B RNA polymerase of HCV. These enzymes are very useful for developing anti-HCV agent since these types of enzymes are not necessary for the host cell but essential for its own replication. In other words, NS5B of HCV {RNA dependent RNA polymerase (replicase)} is an essential enzyme for HCV, and this makes the enzyme a good target for suppressing the replication of HCV.

Now that HCV is not easily treated by vaccine, a new therapy using α-interferon and Ribavirin was introduced. But this, too, caused side effects and was not effective for treating hepatitis C. For example, about 25% of HCV patients showed no reaction to the interferon therapy, and about 25% reacted to it only for temporarily and relapsed into hepatitis C. The rest 50% of the patients maintained ALT at a normal level after the treatment was completed and their HCV RNA became negative. However, 50% of them relapsed into hepatitis C within 3-6 months. In short, only 25% of the HCV patients showed sustained response for more than 6 months. Meanwhile, the most HCV subtype found in patients world wide is 1 (1a, 1b) that is not easily treated by interferon, compared to 2 and 3 subtypes. In case of combination therapy with interferon and ribavirin, the treatment effect was doubled. What is known about ribavirin is that when it was used alone, it showed little effect on HCV and rather, caused side effects like erythroclastic anemia. Thus ribavirin was prescribed only when the interferon therapy was no good or relapsed again. So far, no one actually developed an antiviral agent for treating hepatitis C by suppressing the replication of HCV due to specific action on HCV.

The present invention, therefore, is directed to develop a nonnucleoside compound having little toxicity and side effect but manifesting excellent anti-virus activity against HCV, by researching any possible compound that inhibits the activity of the recombinant HCV RNA polymerase (NS5B, RNA polymerase).

After making so much efforts for developing a compound with excellent anti-virus activity against HCV as an attempt to develop a new HCV therapeutics having little toxicity and side effect, the inventors finally succeeded to synthesize novel 6-(4-substituted-anilino)pyrimidine derivatives represented by the formula I and proved that these compounds are indeed very effective for inhibiting the replication of HCV.

DISCLOSURE OF INVENTION

It is, therefore, an object of the present invention to provide 6-(4-substituted-anilino)pyrimidine derivatives and pharmaceutically acceptable salts thereof, and method for preparing the compounds.

Another object of the present invention is to provide a pharmaceutical composition comprising the above compound as an active ingredient, which has little side effect and is economical, for prevention and treatment of hepatitis C.

To achieve the above objects, the present invention provides novel 6-(4-substituted-anilino)pyrimidine derivatives, represented by the following formula I:

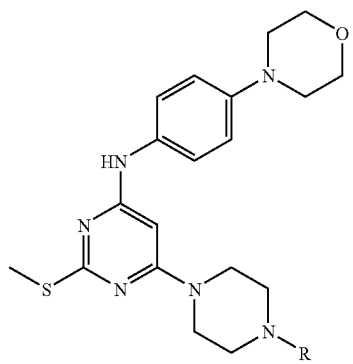

I or pharmaceutically acceptable salts thereof in which R represents a $C_1$-$C_4$ straight or branched alkoxycarbonyl group, heterocycliccarbonyl group or carboxyalkyl group.

Preferably, R in the Formula I is isopropoxycarbonyl group, (3-pyridyl)carbonyl group, (4-pyridyl)carbonyl group or carboxymethyl group.

As aforementioned, the above compounds can be used in form of pharmaceutically acceptable salts. As for that salts, an acid addition salts that are prepared by pharmaceutically acceptable free acids are available. The compounds with the chemical formula I can make pharmaceutically acceptable acid addition salts following the conventional method in the related art. As for free acids, both organic acids and inorganic acids can be used. For instance, inorganic acids include hydrochloric acid, hydrobromic acid, sulfuric acid, and phosphoric acid. Organic acids include citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid or aspartic acid.

In another aspect, the present invention provides a method for preparing 6-(4-substituted-anilino)pyrimidine derivatives, represented by the following scheme.

Scheme (I)

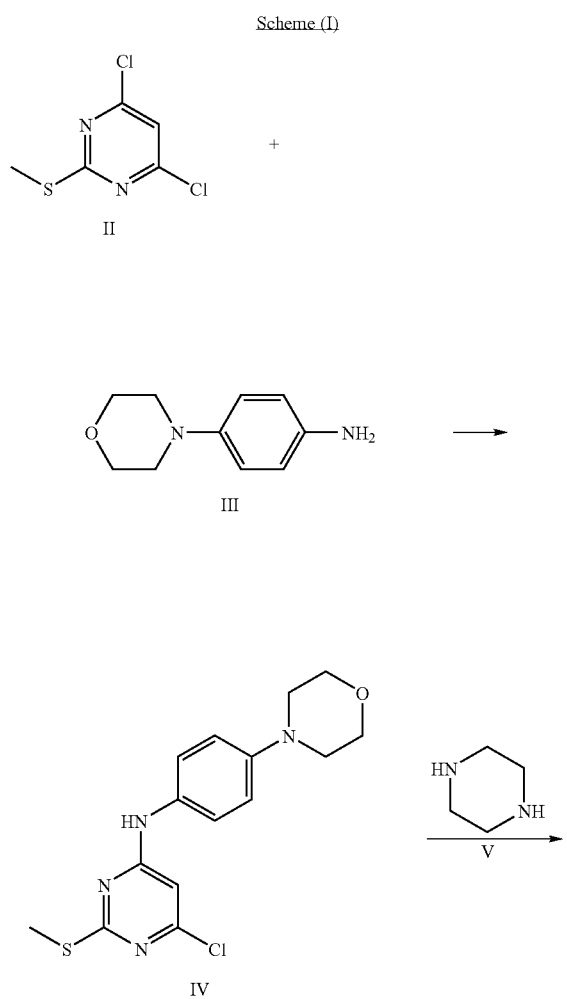

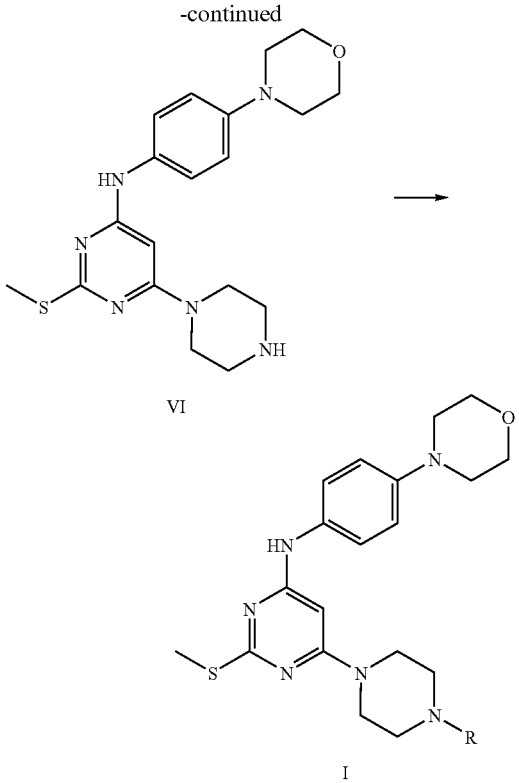

in which R represents a $C_1$-$C_4$ straight or branched alkoxycarbonyl group, heterocycliccarbonyl group or carboxyalkyl group.

As shown in the above scheme (1), the method for preparing a 6-(4-substituted-anilino)pyrimidine derivatives according to the present invention comprises the steps of: (i) reacting 4,6-dichloro-2-(methylthio)pyrimidine of Formula II with 4-(4-morpholino)aniline of Formula III to form an intermediate of 2-methylthio-6-[4-(4-morpholino)anilino]4-chloropyrimidine of Formula IV; (ii) reacting the intermediate of Formula IV prepared in the step (i) with piperazine of Formula V to form an intermediate of 2-methylthio-6-[4-(4-morpholino)anilino]-4-(piperazin-1-yl)pyrimidine of Formula VI; and (iii) reacting the intermediate of Formula VI prepared in the step (ii) with appropriate halogen compounds to form 6-(4-substituted-anilino)pyrimidine derivatives of the present invention.

4,6-dichloro-2-(methylthio)pyrimidine, 4-(4-morpholino) aniline, piperazine and halogen compounds used as starting materials and reactants in the scheme (I) are commercially available. The halogen compounds used in the step (iii) is appropriate reagents to introduce substituents to target compounds and can be suitably selected, depending on substituents to be introduced, by a person possessing ordinary knowledge in the art.

To give more details on the steps (i) and (ii) of the preparation method described above, the reactions are performed in an organic solvent such as methanol, ethanol, isopropanol, dichloromethane, chloroform, acetonitrile, N,N-dimethylformamide, acetone and the like, and in the presence of an organic base such as triethylamine, N,N-diisopropylethylamine, N-methylmorpholine, 1-methylpiperidine, pyridine, 2,6-lutidine, 4-dimethylaminopyridine, N,N-dimethylaniline and the like. The reaction is completed within 12 to 45 hours at a temperature in the range of 40-65° C.

To give more details on the step (iii) of the preparation method described above, the reaction is performed in an organic solvent such as dichloromethane, chloroform, acetonitrile, N,N-dimethylformamide and the like, and in the presence of an organic base such as triethylamine, N,N-diisopropylethylamine, N-methylmorpholine, 1-methylpiperidine, pyridine, 2,6-lutidine, 4-dimethylaminopyridine, N,N-dimethylaniline and the like. The reaction is completed within 1 hour at a temperature in the range of 0-10° C., or within 12 hours at a temperature in the range of 40-80° C., depending on kinds and reactivities of halogen compounds.

The present invention also provides the pharmaceutical compositions for treatment and prevention of hepatitis C, which contains the 6-(4-substituted-anilino)pyrimidine derivatives represented by the chemical formula I and/or its pharmaceutically acceptable salts as an active ingredient.

The compounds of the chemical formula I as the therapeutics for hepatitis C may be administered orally as well as through other routes in clinical uses, and can be used in the form of general drugs. If it needs to be prepared, a generally used diluent including filler, builder, binder, humectant, dis-integration agent or surfactant, or excipient can be employed. In the meantime, the solid preparation for oral administration includes tablets, pills, powder, granules or capsules. This solid preparation involves more than one compound of the chemical formula I and more than one excipient, for example, starch, calcium carbonate, sucrose or lactose, or gelatin. As for the liquid preparation for oral administration, suspension, solution, oily medicine or syrup can be used, but it can also employ a simple diluent, namely water, liquid paraffin, or other kinds of excipient, e.g. humectant, sweetening agent, odorant, or preservative. As for liquid preparation for non-oral administration, sterilized water solution, non-aqueous solvent, suspension or oily medicine. Preferably used non-aqueous solvent and suspension is propylene glycol, polyethylene glycol, vegetable oil like olive oil, and injectable esters like ethyl oleate.

The effective dose of the compound of the chemical formula I is controlled depending on the patient's sex, age and condition. In general, it can be dosed to adults 10 to 1000 mg/day, more preferably 20 to 500 mg/day, or once to three times dividedly per day.

DETAILED DESCRIPTION OF THE PREFERRED EMBODIMENT

Now, the present invention is explained in detail by the following examples. However, the examples are provided for illustration of the present invention not for limitation thereof.

Preparation 1: Preparation of 2-methylthio-6-[4-(4-morpholino)anilino]-4-chloropyrimidine 5.85 g of 4,6-dichloro-2-(methylthio)pyrimidine, 5.35 g of 4-(4-morpholino)aniline and then, 5.1 mL of triethylamine were added in sequence to 80 mL of methanol and heated to 55-60° C. for 18 hours. The reaction mixture was cooled to 20° C., stirred for 2 hours, filtered and washed with 25 mL of methanol to give a crystalline product. The product was dried in vacuo at 30-40° C. to give 8.79 g of the desired compound (87% yield).

m.p.: 159-161° C.

$^1$H-NMR (CDCl$_3$), ppm: δ 2.51 (s, 3H), 3.15 (t, 4H), 3.86 (t, 4H), 6.19 (d, 1H), 6.76 (s, 1H), 6.91 (d, 2H), 7.16 (d, 2H)

Preparation 2: Preparation of 2-methylthio-6-[4-(4-morpholino)anilino]-4-(piperazin-1-yl)pyrimidine 5.6 g of 2-methylthio-6-[4-(4-morpholino)anilino]-4-chloropyrimidine, prepared in Preparation 1, 14.3 g of anhydrous piperazine and then 2.6 mL of triethylamine were added in sequence to 80 mL of methanol and heated to 55-60° C. for 40 hours. The reaction mixture was cooled to 20° C., stirred for 2 hours, filtered and washed with 25 mL of methanol to give a crystalline product. The product was dried in vacuo at 30-40° C. to give 6.17 g of the desired compound (96% yield).

m.p.: 232-234° C.

$^1$H-NMR (DMSO-d$_6$), ppm: δ 2.39 (d, 3H), 2.70 (brs, 4H), 3.02 (brs, 4H), 3.35 (brs, 4H), 3.70 (m, 4H), 5.53 (s, 1H), 6.87 (d, 2H), 7.34 (d, 2H), 8.78 (s, 1H)

EXAMPLE 1
Preparation of 2-methylthio-6-[4-(4-morpholino)anilino]-4-[4-(isopropoxycarbonyl)piperazin-1-yl]pyrimidine 1 g of 2-methylthio-6-[4-(4-morpholino)anilino]-4-(piperazin-1-yl)pyrimidine and 0.4 mL of triethylamine were added in sequence to 40 mL of dichloromethane, stirred for 10 minutes to dissolve completely and cooled to 0° C. 2.85 mL of isopropyl chloroformate (1.0 M in toluene) was slowly added at 0-5° C. and the reaction mixture was stirred for 20 minutes at 0-5° C. 40 mL of water was added and stirred at 20° C. for 10 minutes. The organic layer was separated and washed once with 40 mL of water, concentrated under reduced pressure. The residue was crystallized by 30 mL of ethyl ether, stirred for 2 hours at room temperature and filtered to give a product. The product was washed with 5 mL of ethyl ether and dried in vacuo at 30-40° C. to give 1.05 g of the desired compound (86% yield).

m.p.: 155-157° C.

$^1$H-NMR (CDCl$_3$), ppm: δ 1.23 (d, 6H), 2.48 (s, 3H), 3.15 (brs, 4H), 3.50 (brs, 8H), 3.85 (t, 4H), 4.93 (m, 1H), 5.41 (s, 1H), 6.42 (s, 1H), 6.90 (d, 2H), 7.15 (d, 2H)

EXAMPLE 2
Preparation of 2-methylthio-6-[4-(4-morpholino)anilino]-4-[4-[(3-pyridyl)carbonyl]piperazin-1-yl]pyrimidine 1 g of 2-methylthio-6-[4-(4-morpholino)anilino]4-(piperazin-1-yl)pyrimidine and 0.8 mL of triethylamine were added in sequence to 40 mL of dichloromethane, stirred for 10 minutes to dissolve completely and cooled to 0° C. 0.48 g of nicotinoyl chloride hydrochloride was slowly added at 0-5° C. and the reaction mixture was stirred for 30 minutes at 0-5° C. 40 mL of water was added and stirred at 20° C. for 10 minutes. The organic layer was separated and washed once with 40 mL of water, concentrated under reduced pressure. The residue was crystallized by a co-solvent of 4 mL of dichloromethane and 40 mL of ethyl ether, stirred for 2 hours at room temperature and filtered to give a solid product. The product was washed with 5 mL of ethyl ether and dried in vacuo at 30-40° C. to give 1.13 g of the desired compound (89% yield).

m.p.: 131-133° C.

$^1$H-NMR (CDCl$_3$), ppm: δ 2.47 (d, 3H), 3.15 (brs, 4H), 3.49 (m, 6H), 3.86 (m, 6H), 5.43 (s, 1H), 6.89 (d, 2H), 7.15 (d, 2H), 7.35 (t, 1H), 7.75 (dd, 1H), 8.67 (d, 2H)

EXAMPLE 3
Preparation of 2-methylthio-6-[4-(4-morpholino)anilino]-4-[4-[(4-pyridyl)carbonyl]piperazin-1-yl]pyrimidine The desired compound was prepared by following the same procedure with Example 2, except that isonicotinoyl chloride hydrochloride was substituted for nicotinoyl chloride hydrochloride.

Yield: 93% m.p.: 155-156° C.

$^1$H-NMR (CDCl$_3$), ppm: δ 2.47 (d, 3H), 3.15 (brs, 4H), 3.41 (brs, 2H), 3.57 (brs, 4H), 3.85 (m, 6H), 5.42 (s, 1H), 6.50 (s, 1H), 6.91 (brs, 2H), 7.15 (brs, 2H), 7.28 (m, 2H), 8.70 (d, 2H)

EXAMPLE 4

Preparation of 2-methylthio-6-[4-(4-morpholino) anilino]-4-[4-(carboxymethyl)piperazin-1-yl]pyrimidine Step 1: Preparation of 2-methylthio-6-[4-(4-morpholino)anilino]-4-[4-(ethoxycarbonylmethyl)piperazin-1-yl]pyrimidine 3 g of 2-methylthio-6-[4-(4-morpholino)anilino]-4-(piperazin-1-yl)pyrimidine prepared in Preparation 2, 0.9 mL of ethyl chloroacetate and 1.3 mL of triethylamine were added in sequence to 50 mL of acetonitrile and heated. The reaction mixture was stirred at 70-80° C. for 7 hours. Then, the reaction mixture was slowly cooled to 20° C. and 30 mL of methanol was added, stirred for 1 hour and filtered to give a solid product. The product was washed with 15 mL of methanol and dried in vacuo at 35-45° C. to give 3.41 g of the desired compound (93% yield).

m.p.: 88-90° C.

$^1$H-NMR (DMSO-d$_6$), ppm: δ 1.16 (m, 3H), 2.39 (d, 3H), 3.02 (brs, 4H), 3.15 (m, 2H), 3.35 (d, 4H), 3.44 (brs, 4H), 3.70 (d, 4H), 4.04 (m, 2H), 5.56 (d, 1H), 6.87 (m, 2H), 7.34 (d, 1H), 7.37 (d, 1H), 8.82 (s, 1H)

Step 2: Preparation of 2-methylthio-6-[4-(4-morpholino)anilino]4-[4-(carboxylmethyl)piperazin-1-yl]pyrimidine 2.5 g of 2-methylthio-6-[4-(4-morpholino)anilino]-4-[4-(ethoxycarbonylmethyl)piperazin-1-yl]pyrimidine prepared in the step 1, 25 mL of water and 5.3 mL of 3N aqueous sodium hydroxide solution were added in sequence to 30 mL of methanol and heated. The reaction mixture was stirred at 50-60° C. for 1 hour. Then, the reaction mixture was slowly cooled, and 3N hydrochloric acid was added to adjust pH to 6.0 to 7.0 at 10-20° C. The mixture was stirred for 1 hour and filtered to give a solid product. The product was washed with 20 mL of water and dried in vacuo at 40-50° C. to give 2.24 g of the desired compound (95% yield).

m.p.: 156-158° C.

$^1$H-NMR (DMSO-d$_6$), ppm: δ 2.39 (d, 3H), 2.62 (brs, 4H), 3.02 (brs, 4H), 3.20 (s, 2H), 3.47 (brs, 4H), 3.71 (m, 4H), 5.57 (s, 1H), 6.87 (d, 2H), 7.34 (d, 2H), 8.84 (s, 1H)

EXPERIMENTAL EXAMPLE 1

Test of Inhibitory Effect on Activity of HCV RNA Polymerase (RNA Dependent RNA Polymerase, NS5B) in vitro The following in vitro experiments were conducted to examine the inhibitory effect of the compounds according to the present invention on the activity of HCV RNA dependent RNA Polymerase.

Construct of Recombinant HCV RNA Polymerase

The HCV RNA polymerase was prepared as follows.

HCV cDNA was obtained from the blood of HCV-1b type HCV patient and the NS5B region (1773 bps) was amplified by PCR and cloned into pVLHIS, a baculovirus transfer vector, to prepare a recombinant transfer vector. The prepared transfer vector and the wild-type AcNPV vector were cotransfected into Sf9 insect cell line to yield a recombinant baculovirus containing the histidine-tagged recombinant vector pVLHIS-NS5B. Sufficiently cultured insect cells were infected with the resulting recombinant baculovirus and cultured in Grace's medium containing 10% FBS for 3 to 4 days. The culture broth was centrifuged to obtain only the infected cells. The cells were washed three times with PBS and resuspended in binding buffer [50 mM Na-phosphate (pH 8.0), 30 mM NaCl, 10 mM imidazole, 1 mM DTT, 10% glycerol, 1% NP40], sonicated and the clearized lysate was obtained. Recombinant NS5B was purified by affinity column chromatography using a Ni-NTA His bind resin (Novagen) to produce pure NS5B protein. The (His)$_6$-tagged NS5B was bound to Ni-NTA resin and washed the binding buffer containing 50 mM imidazole. The bound NS5B was eluted with the binding buffer containing imidazole in a step-gradient manner (100-300 mM). The NS5B protein fractions were dialyzed against buffer [50 mM Tris-HCl, 50 mM NaCl, 1 mM DTT, 5 mg MgCl$_2$, 10% glycerol], followed by at −70° C. in a small aliquot.

Construct of RNA Template Containing HCV 3' End (3'-UTR)

The RNA template containing HCV 3' end (3'-UTR) was prepared as follows.

The 3'UTR cDNA (220 bp) of HCV was obtained from 1b HCV RNA of the blood of a hepatitis C patient by PCR and cloned into pcDNA3 vector. Linearized DNA fragment containing the 3'-UTR was prepared using the restriction enzyme Eco RI and used as a template for in vitro transcription using T7 RNA ploymerase to prepare RNA fragment containing 3'-UTR.

Measurement of Inhibitory Activity of Compounds of the Present Invention on Recombinant HCV RNA Polymerase in vitro In vitro inhibitory activity of the compounds of the present invention on recombinant HCV RNA polymerase was measured as follows.

A streptavidin-coated well plate was prepared suitable for the sample to be examined. 25 μl of 2× assay buffer [50 mM Tris-Cl (pH 7.5), 100 mM NaCl, 10 mM MgCl$_2$, 20 mM KCl, 1 mM EDTA, 1 mM DTT] and 10 μl of purified HCV RNA polymerase 200 ng and 3'-UTR template RNA were added to each well. Then, 5 μl of the sample to be examined was added to have final concentrations of 10, 1, 0.1 and 0.01 μg/mL. Finally, 10 μl of a reactant solution containing DIG-(digoxigenin)-UTP, biotin-UTP, ATP, CTP, GTP, and UTP as a nucleotide for the ploymerase reaction with the RNA template of HCV 3'-UTR RNA was added to each well. The reaction mixture was incubated at 22° C. for 60 minutes. By the action of HCV polymerase, newly generated RNAs including UTP conjugated with biotin and DIG were copied and these new RNAs could bind to streptavidin coated on the well by biotin-conjugated UTP. After completion of the reaction, the plate was washed three times with 200 μl of a washing buffer (pH 7.0, Roche Co.) to remove unreacted substances and impurities. Then, 100 μl of the secondary antibody anti-DIG-POD (peroxidase, Roche Co.) was added to each well and incubated at 37° C. for 1 hour. Again, the well plate was washed with the washing buffer. Finally, 100 μl of ABTS$^R$ (Roche Co.) as a POD substrate was added to each well and reacted for 15 to 30 minutes. The optical density (OD) was measured using an ELISA reader (Bio-Tek instrument Co.) at 405 nm. The inhibitory effect on the activity of HCV polymerase was calculated by subtracting the OD of the positive control without the sample. The results are shown in Table 1 below.

TABLE 1

| Test compound | Substituent (R) | Inhibition of activity of HCV RNA polymerase (%) | | | |
|---|---|---|---|---|---|
| | | 10 μg/mL | 1 μg/mL | 0.1 μg/mL | 0.01 μg/mL |
| Example 1 | Isopropoxycarbonyl | 99 | 81 | 55 | 29 |
| Example 2 | (3-pyridyl)carbonyl | 98 | 62 | 30 | 15 |
| Example 3 | (4-pyridyl)carbonyl | 93 | 73 | 53 | 23 |
| Example 4 | carboxymethyl | 94 | 65 | 52 | 27 |

As can be seen from the above table, it is proved that the compounds according to the present invention show excellent inhibitory effects on activity of HCV RNA polymerase which plays an important role in reproduction of HCV, thereby inhibiting replication of HCV by this property. Also, the compounds according to the present invention can be advantageously used as a therapeutic or prophylactic agent of C type hepatitis.

EXPERIMENTAL EXAMPLE 2
Cytotoxicity Assy

The cytotoxicity of the compounds of Formula I was examined by the MTT assay, one of well known in vitro toxicology assay methods, using Hep G2 cells. As a result, all the compounds used in the experiment were found to have $CC_{50}$ of greater than 100 μg/mL, indicating that they are safe compounds with extremely low cytotoxicity.

INDUSTRIAL APPLICABILITY

As described above, the novel 6-(4-substituted-anilino)pyrimidine derivatives according to the present invention represented by the Formula I have excellent inhibitory effect on replication of hepatitis C virus and low cytotoxicity. Therefore, they can be advantageously used as a therapeutic or prophylactic agent of C type hepatitis.

What is claimed is:

1. A compound of the formula I:

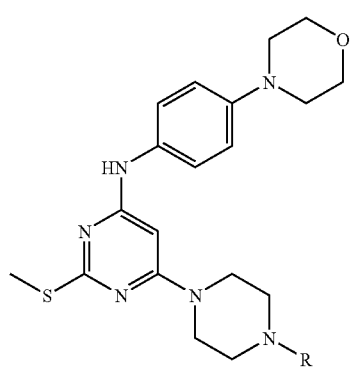

I or pharmaceutically acceptable salts thereof in which R represents a C1-C4 straight or branched alkoxycarbonyl group, heterocycliccarbonyl group or carboxyalkyl group.

2. The compound according to claim 1 or pharmaceutically acceptable salts thereof in which R is one selected from the group consisting of isopropoxycarbonyl group, (3-pyridyl)carbonyl group, (4-pyridyl)carbonyl group and carboxymethyl group.

3. A method for preparing a compound of claim 1, the method comprising the steps of:
    (i) reacting 4,6-dichloro-2-(methylthio)pyrimidine of Formula II with 4-(4-morpholino)aniline of Formula III to form an intermediate of 2-methylthio-6-[4-(4-morpholino)anilino]-4-chloropyrimidine of Formula IV;
    (ii) reacting the intermediate of Formula IV with piperazine of Formula V to form an intermediate of 2-methylthio-6-[4-(4-morpholino)anilino]-4-(piperazin-1-yl)pyrimidine of Formula VI; and
    (iii) reacting the intermediate of Formula VI with appropriate halogen compounds to form the compound of the formula I:

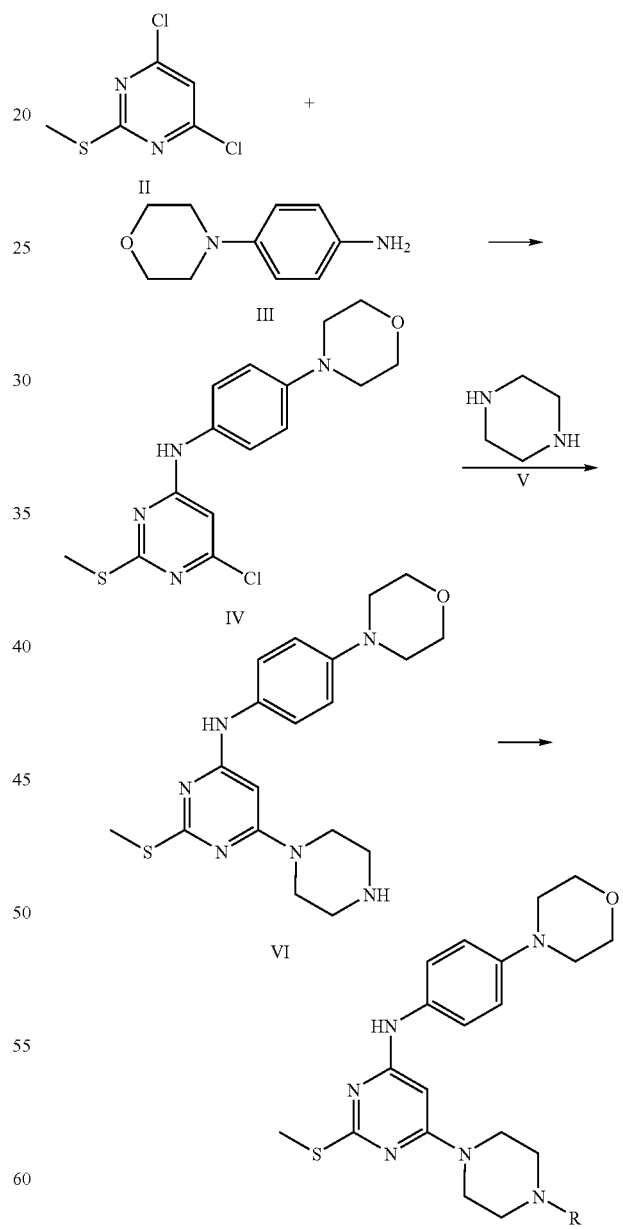

in which R represents a C1-C4 straight or branched alkoxycarbonyl group, heterocycliccarbonyl group or carboxyalkyl group.

* * * * *

UNITED STATES PATENT AND TRADEMARK OFFICE
CERTIFICATE OF CORRECTION

PATENT NO. : 7,276,501 B2
APPLICATION NO. : 10/508306
DATED : October 2, 2007
INVENTOR(S) : Jong-Woo Kim et al.

It is certified that error appears in the above-identified patent and that said Letters Patent is hereby corrected as shown below:

Col. 10, line 9, delete "centriftiged" and replace with -- centrifuged --

Signed and Sealed this

Eighteenth Day of March, 2008

JON W. DUDAS
*Director of the United States Patent and Trademark Office*